US00PP15704P2

(12) United States Plant Patent
Hanes

(10) Patent No.: US PP15,704 P2
(45) Date of Patent: Mar. 29, 2005

(54) ***VERBENA* PLANT NAMED 'RAP PUREY TWO'**

(50) Latin Name: ***Verbena hybrida*×*Verbena tenuisecta***
Varietal Denomination: Rap Purey Two

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 35 days.

(21) Appl. No.: 10/818,495

(22) Filed: Apr. 5, 2004

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of *Verbena* plant named 'Rap Purey Two', characterized by its compact, low and outwardly spreading, and decumbent plant habit; freely branching habit; early and uniform flowering habit and violet-colored flowers with distinct white-colored centers.

1 Drawing Sheet

Botanical classification/cultivar designation: *Verbena hybrida*×*Verbena tenuisecta* cultivar Rap Purey Two.

BACKGROUND OF THE INVENTION

The present Invention relates to a new and distinct cultivar of *Verbena* plant, botanically known as *Verbena hybrida*×*Verbena tenuisecta*, and hereinafter referred to by the name 'Rap Purey Two'.

The new *Verbena* is a product of a planned breeding program conducted by the Inventor in Gilroy, Calif. The objective of the breeding program is to develop new compact *Verbena* cultivars with early and uniform flowering, good basal branching, attractive flower and foliage coloration, and tolerance to Powdery Mildew.

The new Verbena originated from a cross-pollination made by the Inventor in February, 2000 of the *Verbena hybrida* cultivar Morena, disclosed in U.S. Plant Pat. No. 11,231, as the female, or seed, parent with a proprietary *Verbena hybrida*×*Verbena tenuisecta* selection identified as code number 99-843-4, not patented, as the male, or pollen, parent. The cultivar Rap Purey Two was discovered and selected by the Inventor as a flowering plant within the progeny from this cross-pollination in a controlled environment in Gilroy, Calif. in October, 2000.

Asexual reproduction of the new cultivar by terminal cuttings in Gilroy, Calif., since October, 2000 has shown that the unique features of this new *Verbena* are stable and reproduced true to type in successive generations of asexual reproduction.

SUMMARY OF THE INVENTION

The following traits have been repeatedly observed and are determined to be the unique characteristics of 'Rap Purey Two'. These characteristics in combination distinguish 'Rap Purey Two' as a new and distinct cultivar:

1. Compact, low and outwardly spreading, and decumbent plant habit.
2. Freely branching habit.
3. Early and uniform flowering habit.
4. Dark violet-colored flowers with distinct white-colored centers.
5. Relatively less susceptible to Powdery Mildew.

In side-by-side comparisons conducted in Gilroy, Calif., plants of the new *Verbena* differed from plants of the female parent, the cultivar Morena, in the following characteristics:

1. Plants of the new *Verbena* were more trailing than plants of the cultivar Morena.
2. Plants of the new *Verbena* and the cultivar Morena differed in flower coloration as plants of the cultivar Morena had pink-colored flowers.

In side-by-side comparisons conducted in Gilroy, Calif., plants of the new *Verbena* differed from plants of the male parent selection in the following characteristics:

1. Plants of the new *Verbena* had narrower leaves than plants of the male parent selection.
2. Plants of the new *Verbena* flowered earlier than plants of the male parent selection.
3. Plants of the new *Verbena* and the male parent selection differed in flower color as plants of the male parent selection had red purple-colored flowers.

The new *Verbena* can be compared to the cultivar, Babylon Carpet Blue, not patented. However, in side-by-side comparisons conducted in Gilroy, Calif., plants of the new *Verbena* differed from plants of the cultivar Babylon Carpet Blue in the following characteristics:

1. Plants of the new *Verbena* had shorter internodes than plants of the cultivar Babylon Carpet Blue.
2. Leaves of plants of the new *Verbena* were larger than leaves of plants of the cultivar Babylon Carpet Blue.
3. Flowers of plants of the new *Verbena* were lighter violet in color than flowers of plants of the cultivar Babylon Carpet Blue.
4. Flowers of plants of the new *Verbena* had distinct white-colored centers whereas flowers of plants of the cultivar Babylon Carpet Blue did not have distinct white-colored centers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Rap Purey Two'.

The photograph at the bottom of the sheet is a close-up view of typical flower racemes and leaves of 'Rap Purey Two'.

Flower and foliage colors in the photographs may differ slightly from the color values cited in the detailed botanical description which accurately describe the colors of the new *Verbena*.

DETAILED BOTANICAL DESCRIPTION

Plants of the cultivar Rap Purey Two have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures about 24 to 32° C., night temperatures about 13 to 18° C. and light levels about 2,000 foot-candles. Plants used for the photographs and description were about twelve weeks from planting rooted cuttings and were pinched twice. In the following description, color references are made to The Royal Horticultural Society Colour Chart, 1995 Edition, except where general terms of ordinary dictionary significance are used.

Botanical classification: *Verbena hybrida*×*Verbena tenuisecta* cultivar Rap Purey Two.

Parentage:

*Female, seed, or parent.*—*Verbena hybrida* cultivar Morena, disclosed in U.S. Plant Pat. No. 11,231.

*Male, or pollen, parent.*—Proprietary *Verbena hybrida*×*Verbena tenuisecta* selection identified as code number 99-843-4, not patented.

Propagation:

*Type cutting.*—Terminal cuttings.

*Time to initiate roots.*—About 7 to 10 days at 22 to 24° C.

*Time to produce a rooted cutting or liner.*—About three to four weeks at 22 to 24° C.

*Root description.*—Fine, fibrous; white in color.

*Rooting habit.*—Freely branching.

Plant description:

*Form.*—Compact, low and outwardly spreading, and decumbent plant habit.

*Growth and branching habit.*—Moderately vigorous and freely-branching with about six main stems and multiple secondary lateral branches.

*Plant height.*—About 11 cm.

*Plant diameter or spread.*—About 51 cm.

*Lateral branches.*—Length: About 34 cm. Diameter: About 2.5 mm. Internode length: Vegetative branches, about 1.75 cm; reproductive branches, about 5 cm. Strength: Strong. Texture: Pubescent. Color: 146A.

*Foliage description.*—Arrangement: Opposite, simple. Length: About 3.4 cm. Width: About 3.2 cm. Shape: Deltoid; highly dissected, fern-like. Apex: Acute. Base: Attenuate. Margin: Deeply dissected. Texture, upper and lower surfaces: Coarse, pubescent. Venation pattern: Pinnate, netted. Color: Developing and fully expanded foliage, upper surface: 147A. Developing and fully expanded foliage, lower surface: 147B. Venation, upper and lower surfaces: 147B. Petiole: Length: About 8 mm. Diameter: About 2 mm. Color: 147A.

Flower description:

*Flower type and habit.*—Single upright salverform flowers arrangement on terminal racemes; flowers sessile. Freely flowering with about 56 flowers per raceme; about three racemes per lateral branch. Inflorescences positioned above and beyond the foliage. Flowers last about five to seven days under greenhouse conditions. Flowers not persistent.

*Fragrance.*—None detected.

*Flowering season.*—In the garden, flowering is continuous from spring until fall.

*Inflorescence size.*—Height: About 5 cm. Diameter: About 3.8 cm.

*Flower size.*—Diameter: About 1.3 cm. Tube length: About 1.8 cm.

*Flower buds.*—Length: About 1.1 cm. Diameter: About 2 mm. Shape: Tubular. Color: 83C.

*Petals.*—Quantity/arrangement: Five per flower fused at base. Lobe length: About 6 mm. Lobe width: About 4 mm. Shape: Cordate. Apex: Emarginate. Margin: Entire. Texture, upper and lower surfaces: Velvety, smooth. Color: When opening, upper surface: Brighter than 83A. When opening, lower surface: 83C. Fully opened, upper surface: 83A; towards the center, close to 155A. With development, color becoming closer to 83B. Fully opened, lower surface: 83C to 83D. Throat: Close to 155A.

*Sepals.*—Quantity/arrangement: Five, fused into a tube. Length: About 1 cm. Diameter: Less than 1 mm. Shape: Ligulate. Apex: Acuminate. Margin: Entire. Texture, upper and lower surfaces: Coarse, pubescent. Color, upper surface: 148A. Color, lower surface: 148B.

*Peduncles.*—Length: About 5.25 cm. Diameter: About 1 mm. Angle: Upright or curving upward on horizontal stems. Strength: Strong. Color: 146A.

*Reproductive organs.*—Stamens: Quantity: Four. Anther shape: Ovoid. Anther length: Less than 1 mm. Anther color: 145B. Pollen amount: Scarce. Pollen color: 154C. Pistils: Quantity: One. Pistil length: About 1.3 cm. Stigma shape: Bi-parted. Stigma color: 145B. Style length: About 1.1 cm. Style color: 145D. Ovary color: 145B.

*Fruit/seed.*—Fruit and seed production has not been observed.

Disease/pest resistance: Plants of the new *Verbena* have been observed to be relatively less susceptible to Powdery Mildew. Plants of the new *Verbena* have not been observed to be resistant to other pathogens and pests common to *Verbena*.

Temperature tolerance: Plants of the new *Verbena* have been observed to be tolerant to temperatures ranging from 2 to 40° C.

It is claimed:

1. A new and distinct cultivar of *Verbena* plant named 'Rap Purey Two', as illustrated and described.

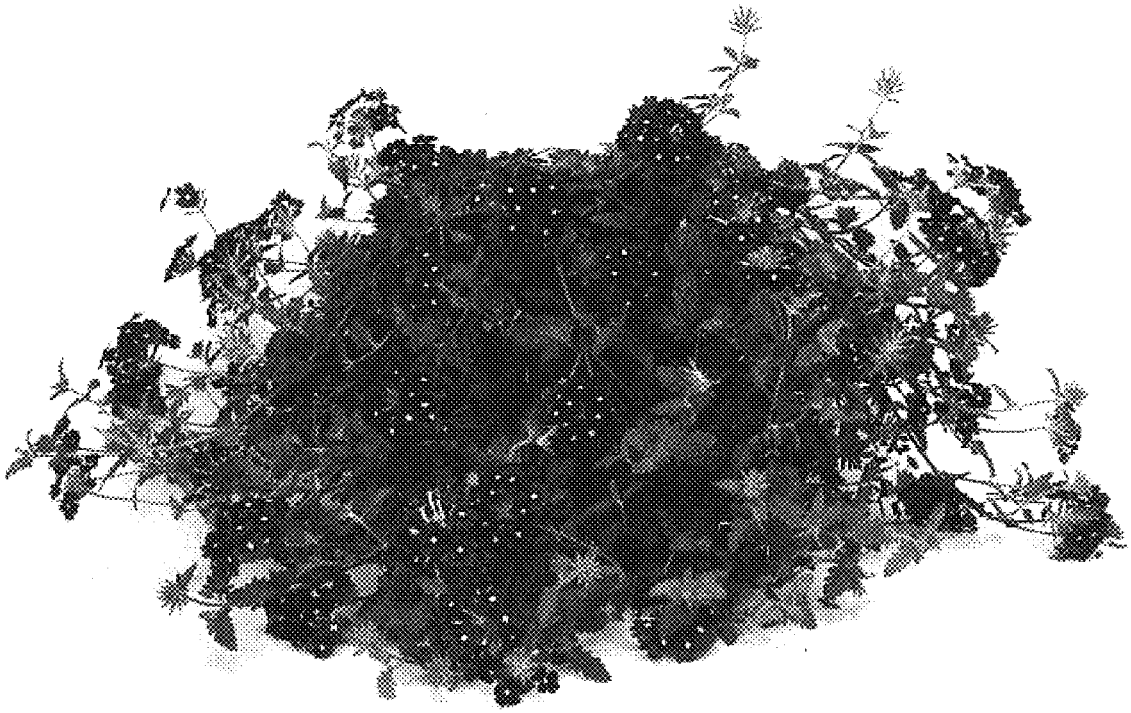
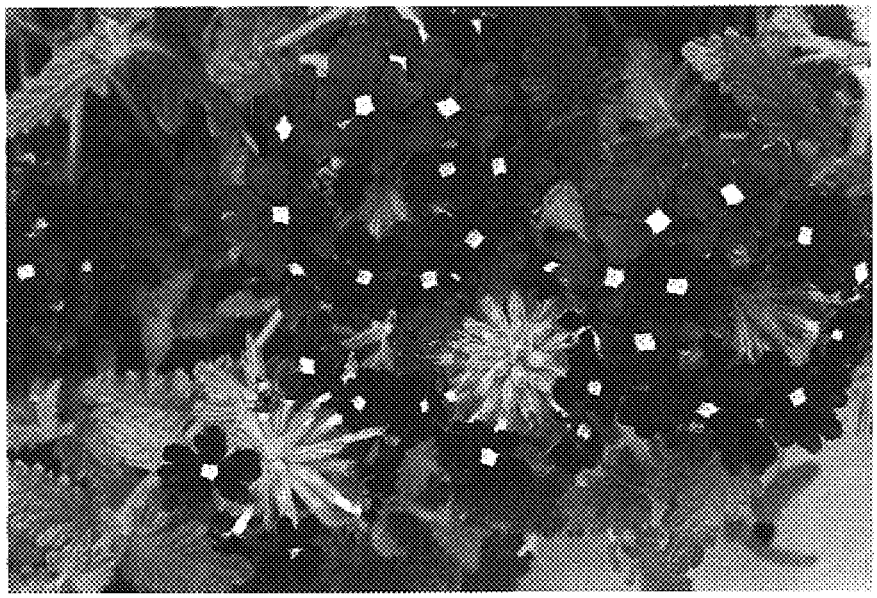

* * * * *